(12) United States Patent
Shiue

(10) Patent No.: US 8,429,797 B2
(45) Date of Patent: Apr. 30, 2013

(54) BUCKLING DEVICE

(75) Inventor: Chih-Cheng Shiue, Taipei (TW)

(73) Assignee: QBAS Co., Ltd. (TW)

( * ) Notice: Subject to any disclaimer, the term of this patent is extended or adjusted under 35 U.S.C. 154(b) by 492 days.

(21) Appl. No.: 12/685,783

(22) Filed: Jan. 12, 2010

(65) Prior Publication Data

US 2011/0030179 A1   Feb. 10, 2011

(30) Foreign Application Priority Data

Aug. 10, 2009  (TW) .............................. 98126724 A

(51) Int. Cl.
*A44B 11/06* (2006.01)
*A44B 11/25* (2006.01)
*A62B 9/04* (2006.01)

(52) U.S. Cl.
USPC ....... 24/170; 2/452; 24/191; 24/625; 24/68 E; 24/193; 351/143

(58) Field of Classification Search .......................... None
See application file for complete search history.

(56) References Cited

U.S. PATENT DOCUMENTS

| 6,457,210 | B1 | 10/2002 | Shirai et al. | |
| 7,836,561 | B2 * | 11/2010 | Vaccaro et al. | 24/68 E |
| 2006/0010585 | A1 | 1/2006 | Chiang | |
| 2006/0230584 | A1 | 10/2006 | Pan | |
| 2008/0244875 | A1 | 10/2008 | Chou | |
| 2009/0100645 | A1 | 4/2009 | Weng | |
| 2009/0276942 | A1 * | 11/2009 | Chiang | 2/452 |

FOREIGN PATENT DOCUMENTS

| CN | 200820134629.5 | 6/2009 |
| FR | 2679342 | 1/1993 |
| GB | 2416598 | 2/2006 |
| JP | 06-237805 | 8/1994 |
| JP | 2001-198236 | 7/2001 |
| JP | 2001-218869 | 8/2001 |
| TW | M340997 | 9/2008 |

OTHER PUBLICATIONS

China Office Action mailed Dec. 16, 2011.
English translation (by machine) of Chinese Office Action mailed Dec. 16, 2011.
English translation of abstract of CN 200820134629.5.
Japan Office Action mailed Mar. 6, 2012.
English translation (by machine) of Japan Office Action mailed Mar. 6, 2012.
English translation of abstract of JP 06-237805.
English translation of abstract of JP 2001-218869.
English translation of abstract of JP 2001-198236.
European search report for EP 10187216.6 mailed Apr. 5, 2012.
European search report for EP 10150956.0 mailed May 8, 2012.
English translation of abstract of FR 2679342.

(Continued)

*Primary Examiner* — Jack W. Lavinder
(74) *Attorney, Agent, or Firm* — McClure, Qualey & Rodack, LLP

(57) ABSTRACT

A buckling device for fastening a belt is provided. The buckling device comprises a first portion, a second portion and an elastic portion. The elastic portion is made of a material with a shore hardness substantially between A10 and A95. The elastic portion contacts the first portion and the second portion, so that the second portion engages with the belt and the belt is fastened.

14 Claims, 16 Drawing Sheets

OTHER PUBLICATIONS

English translation of abstract of TW M340997.
Taiwan Office Action mailed Jun. 29, 2012.
English translation of Taiwan Office Action mailed Jun. 29, 2012.
China Office Action mailed Aug. 10, 2012.
English translation (by machine) of China Office Action mailed Aug. 10, 2012.

* cited by examiner

BUCKLING DEVICE

This application claims priority to Taiwan Invention Application No. 098126724 filed on Aug. 10, 2009, the disclosures of which are incorporated herein by reference in their entirety.

CROSS-REFERENCES TO RELATED APPLICATIONS

Not applicable.

BACKGROUND OF THE INVENTION

1. Field of the Invention

The present invention relates to a buckling device, and in particular to a buckling device employing a high flexibility material as the elastic portion of the buckling device.

2. Descriptions of the Related Art

Masks, such as goggles, diving mask or other devices that cover the face of the wearer, and diving fins are commonly used with many water activities. In general, the mask and the diving fin both have a buckling device and a belt. The wearer adjusts the length of the belt based on the size of the wearer. After the belt is adjusted, the buckling device secures the belt and the belt winds around the wearer.

FIGS. 1A to 1C show a conventional buckling device 1 comprising a body 11, a snap-fitting element 12 and a restoration element 13, a first pivot 17 and a second pivot 16. The snap-fitting element 12 comprises an engaging end 15 and an opposite end 14. The opposite end 14 comes in contact with the restoration element 13 while the engaging end 15 engages a belt (not shown in the figures), which is bent and wound around a pivot 16. When the wearer lifts up the snap-fitting element 12, the opposite end 14 rotates inwards along the first pivot 17 (i.e., the snap-fitting element 12 in FIG. 1C rotates counterclockwise) to press the restoration element 13 and causes the restoration element 13 to deform outwards. The restoration element 12 will generate a pre-pressed elastic restoration force. The engaging end 15 will protrude upwards to disengage with the belt of the mask or the diving fin. In that instant, the wearer can adjust the length of the belt based on the size of the wearer such that the mask or the diving fin can be secured according to the size of the wearer. When the wearer exerts a force onto the opposite end 14, in most cases, the restoration element 13 must be of sufficient strength due to the integrally formed restoration element 13 and the body 11, and because of this, the material of the restoration element 13 does not have sufficient flexibility. Thus, the wearer cannot swiftly disengage the snap-fitting element 12 outwards, and the wearer requires some strength to adjust the belt. The restoration element 13 may not have sufficient flexibility and after repeated use of the restoration element 13, the material of the element 13 may become fatigued or fragile.

FIGS. 2A to 2C illustrate another prior art buckling device 2. The buckling device 2 comprises a body 21, a snap-fitting element 22 and at least one push portions, wherein the least one push portions are two push portions 24. The body 21 comprises a pivot 26, a belt for a mask or a diving fin, etc (not shown) which is adapted to bend around the pivot 26. The snap-fitting element 22 comprises a snap-fitting protrusion 23 and an engaging end 25. The two push portions 24 are disposed onto the two lateral sides (as shown in FIGS. 2A and 2B) of the snap-fitting element 22 along the axial direction of the pivot 26. The engaging end 25 is disposed at one lateral side of the snap-fitting element 22 which is closer to the pivot 26, and engages the belt (not shown) winding around the pivot 26. The snap-fitting protrusion 23 of the snap-fitting element 22 is engaged at a hole formed on the body 21 such that the snap-fitting element 22 acquires a restoration force.

When the two push portions 24 are simultaneously subjected to inwards pressure, the two sides of the snap-fitting element 22 are forced to protrude outwards, and the gap between the engaging end 25 and the belt of the mask or the diving fin, etc increases. In that instant, the length of the belt can be adjusted based on the size of the wearer, and the belt winds around the wearer such that the mask or the diving fin is comfortably fastened onto the wearer. When the wearer releases the push portion 24, the snap-fitting element 22, as a result of the restoration force of the snap-fitting protrusion 23, returns to its original position and forces the push portion 24 to also return to their original position. Similar to the above-described buckling device 1, the snap-fitting protrusion 23 and the snap-fitting element 22 are formed integrally. As a result, the buckling device has to have sufficient strength and hardness to engage with the belt. Thus, if the material of the snap-fitting element 23 is too hard, it does not have sufficient flexibility, which will cause that the snap-fitting element 22 can not be pushed out swiftly by the wearer. This will cause the wearer in the course of adjusting the belt to use extra strength to push the snap-fitting element. In addition, after the snap-fitting protrusion 23 of the conventional buckling device 2 is used repeatedly, the snap-fitting protrusion 23 will become fragile and may break. Thus, when the belt is engaged, it does not have a sufficient engaging force, and the engaging end 25 and the belt are not securely fastened. If the belt is dislocated, the wearer may face safety problem to his life.

In view of this, it is desired in the art to provide a buckling device that can be controlled swiftly, and provide firmer engagement and prevent the problem of fatigue and fragility.

SUMMARY OF THE INVENTION

The primary objective of this invention is to provide a buckling device which can be easily assembled and non-laboriously and sensitively controlled, and provide firmer engagement. In addition the engagement of the device is assured so that breakage of the device due to fatigue or other problems is prevented.

A buckling device of this invention for securing a belt is provided. The belt has a plurality of second protrusions. The buckling device comprises a first portion, a second portion, and an elastic portion. Therein, the elastic portion is made of a material with a shore hardness substantially between A10 and A95, and is more flexible than the first portion. The elastic portion contacts the first portion and the second portion so that the second portion engages with the belt, and the belt is fastened.

The detailed technology and preferred embodiments implemented for the subject invention are described in the following paragraphs accompanying the appended drawings for people skilled in this field to well appreciate the features of the claimed invention.

DESCRIPTION OF THE PREFERRED EMBODIMENT

Figure 1A:
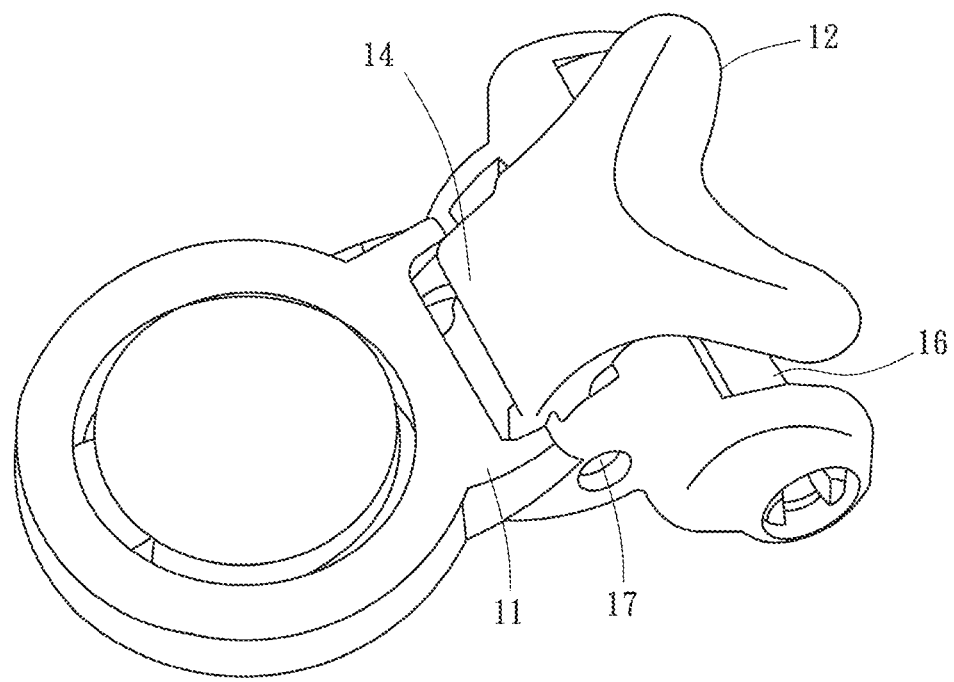
FIG. 1A is a perspective view schematically showing a conventional buckling device.
Figure 1B:
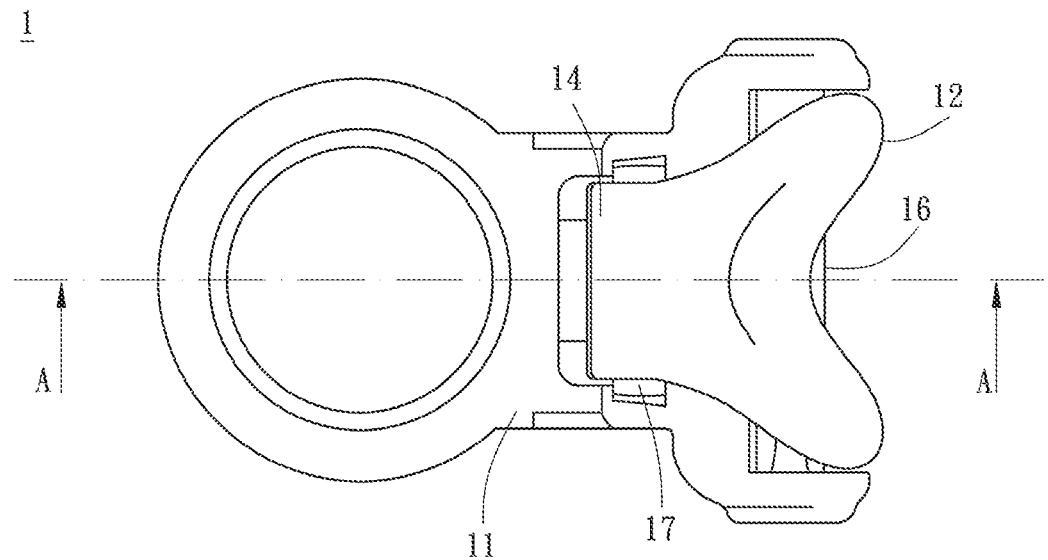
FIG. 1B is a top view of the conventional buckling device shown in FIG. 1A.
Figure 1C:
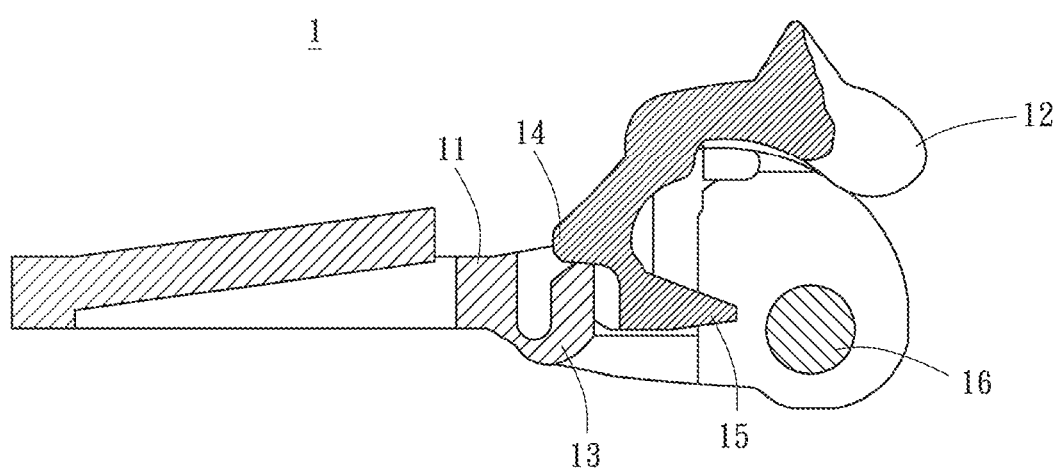
FIG. 1C is a sectional view of the conventional buckling device along line A-A in FIG. 1B.
Figure 2A:
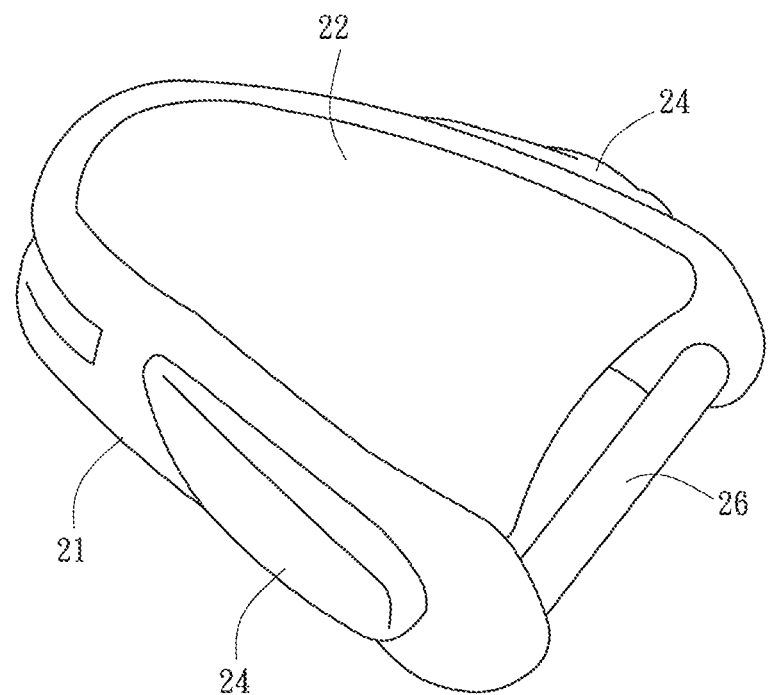
FIG. 2A is a perspective view schematically showing another conventional buckling device.
Figure 2B:
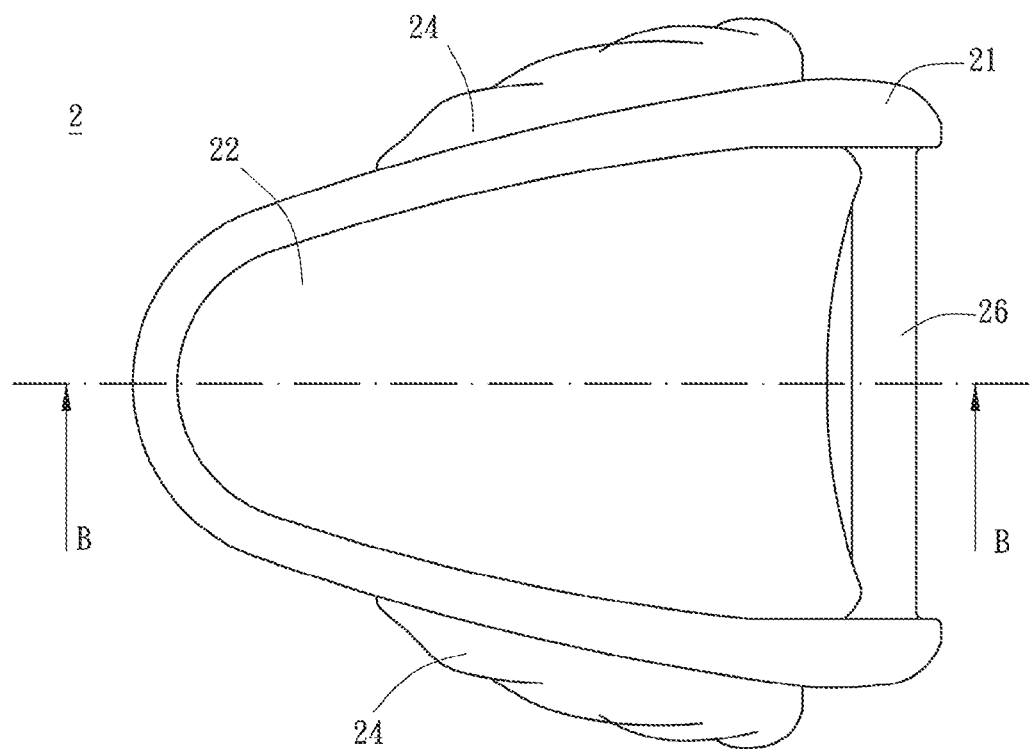
FIG. 2B is a top view of the conventional buckling device shown in FIG. 2A.
Figure 2C:
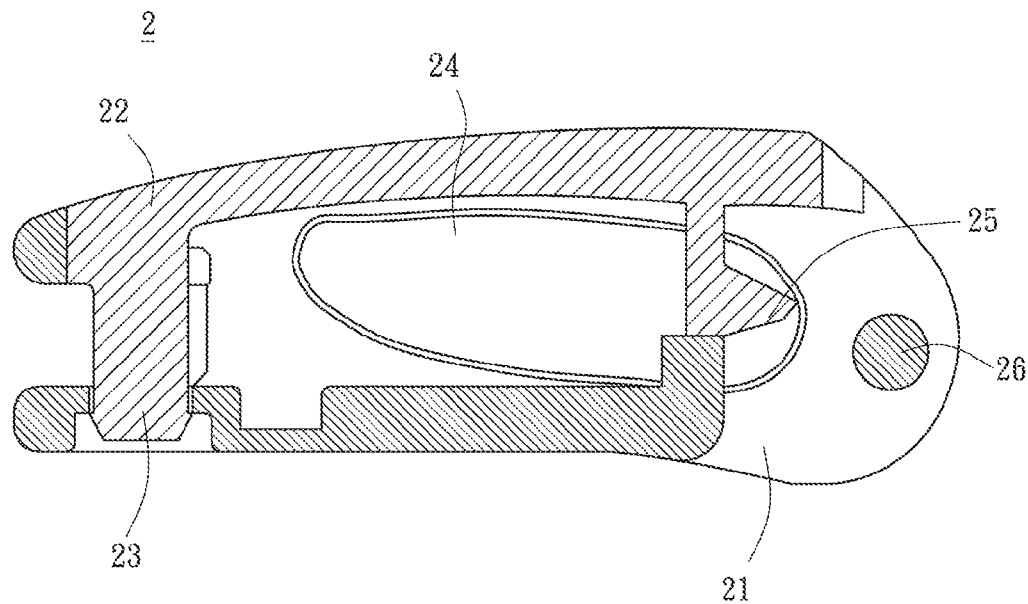
FIG. 2C is a sectional view of the conventional buckling device along line B-B in FIG. 2B.

As shown in FIGS. 3A to 3D, the buckling device 3 for a belt 6 in accordance with the present invention comprises a first portion 31, a second portion 32 and an elastic portion 33. The elastic portion 33 is made of a material which is softer than that of the first portion 31 and has a shore hardness substantially between A10 to A95. The elastic coefficient of the elastic portion 33 is generally smaller than that of the first portion 31, and is substantially lower than 20 Gpa. In other words, the elastic portion 33 in relation to the first portion 31 possesses better flexibility. As compared with the restoration structure of the conventional buckling devices, the elastic portion 33 is easily deformed, and breakage as a result of fatigue in of material will not occur easily. The belt 6 has a plurality of second protrusions 61, while the second portion 32 comprises at least one first protrusion 321. The elastic portion 33 contacts the first portion 31 and the second portion 32, and biases the second portion 32 such that the first protrusion 321 engages with the second protrusions 61 of the belt 6, and the belt 6 is fastened. The elastic portion 33 is made of a material selected from the group consisting of silicone, Thermoplastic Rubber (TPR), Polyvinyl Chloride (PVC) and the combination thereof. The first portion 31 is made of a material selected from the group consisting of Polycarbonate (PC), Alkylbenzene Sulfonate (ABS), Polyoxymethylene (POM), Polypropylene (PP), Thermoplastic Rubber (TPR), Nylon, Polyethylene (PE), Polyurethane (PU) and the combination thereof.

In detail, FIGS. 3A to 3D illustrate the first preferred embodiment of a buckling device 3 in accordance with the present invention. The buckling device 3 further comprises a first pivot 35 and a second pivot 36, wherein the second pivot 36 is fastened with the first portion 31, and the belt 6 winds around the second pivot 36. A plurality of second protrusions 61 of the belt 6 and the second pivot 36 are configured in parallel to the first pivot 35. The second portion 32 of the buckling device 3 has an engaging end 322 and an opposite end 323, and at least one first protrusion 321 is disposed at the engaging end 322 of the second portion 32. The first pivot 35 pivotally connects the first portion 31, the second portion 32 and the elastic portion 33, such that the second portion 32 and the elastic portion 33 rotate with regard to the first portion 31. In the present preferred embodiment, the elastic portion 33 is disposed between the first portion 31 and the second portion 32. The elastic portion 33 biases the opposite end 323 of the second portion 32 outwards, so that the first protrusion 321 is adapted to rotate inwards along the first pivot 35 to push and engage with the second protrusion 61 of the belt to fasten the belt 6.

In further reference to FIGS. 3E to 3H, when the wearer wants to adjust the tightness of the belt 6 of a mask 8 or a diving fin 9, etc, the opposite end 323 of the second portion 32 is continuously pushed such that the opposite end 323 pushes the elastic portion 33 inwards. At the same time, the elastic portion 33 stores an elastic restoration force. In that instant, the engaging end 322 rotates outwards along the first pivot 35 and a gap is formed between the first protrusion 321 and the second protrusions 61 to remove the engaging relationship between the first protrusion 321 of the engaging end 322 and the second protrusions 61 of the belt 6; thus, the wearer can appropriately adjust the belt 6 until an appropriate length is obtained. After the wearer removes the pressure exerted onto the opposite end 323 of the second portion 32, the elastic portion 33 will release the stored elastic restoration force and exert in the opposite direction an outward reaction force to the opposite end 323 of the second portion 32 so that the opposite end 323 receives a force and biases outwards. At that instant, the engaging end 322 in relation to the opposite end 323 rotates inwards and engages the second protrusions 61 of the belt 6. Because the elastic portion 33 in accordance with the present invention is made of a very flexible and soft material, the wearer does not need to use great strength to press the elastic portion 33. Furthermore, the highly flexible elastic portion 33 will not break, become ineffective or fatigue.

FIGS. 4A to 4D illustrate a buckling device 4 of the second preferred embodiment in accordance with the present invention. The buckling device 4, similar to that of the first preferred embodiment, also comprises a first portion 41, a second portion 42 and an elastic portion 43. Similar to the first preferred embodiment, the elastic portion 43 has a shore hardness substantially between A10 and A95, and the elastic coefficient of the elastic portion 43 is smaller than that of the first portion 41 and is below 20 Gpa, i.e., the elastic portion 43, as opposed to the first portion 41, has better flexibility. The material of the elastic portion 43 of the present preferred embodiment is similar to that of the first preferred embodiment and is selected from the group consisting of silicone, Thermoplastic Rubber (TPR), Polyvinyl Chloride (PVC) and the combination thereof. The material of the first portion is selected from the group consisting of Polycarbonate (PC), Alkylbenzene sulfonate (ABS), Polyoxymethylene (POM), Polypropylene (PP), Thermoplastic Rubber (TPR), Nylon, Polyethylene (PE), Polyurethane (PU) and the combination thereof.

Figure 4A:
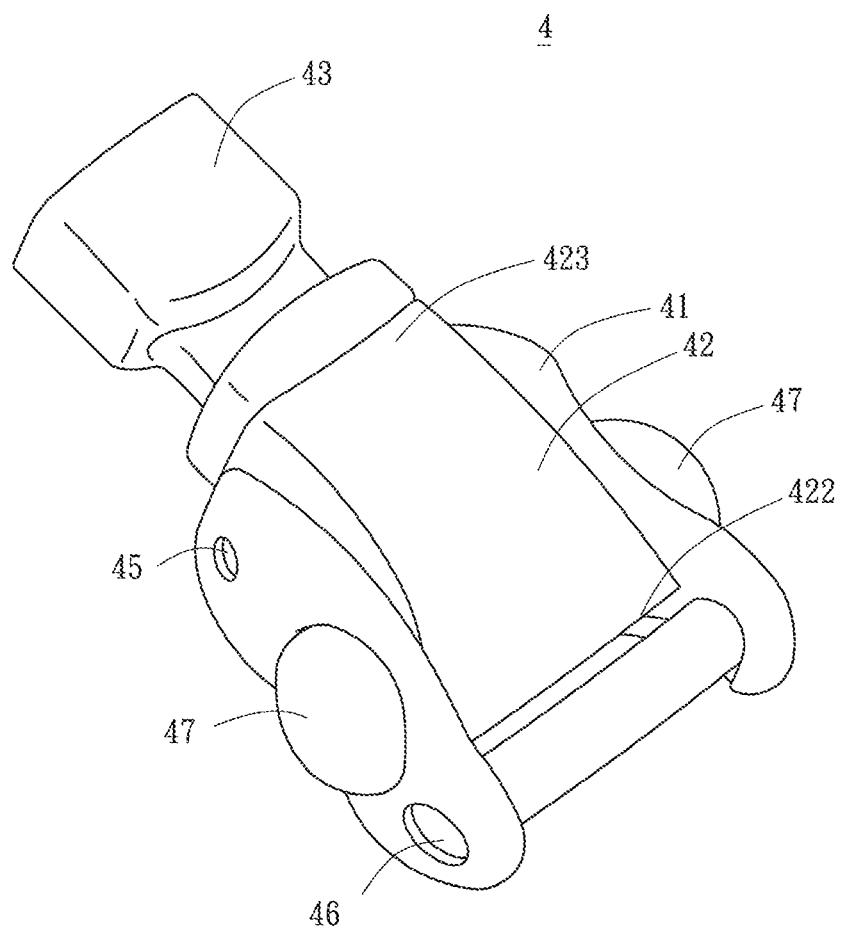
FIG. 4A is a perspective view of a buckling device of a second preferred embodiment of the present invention.
Figure 4B:
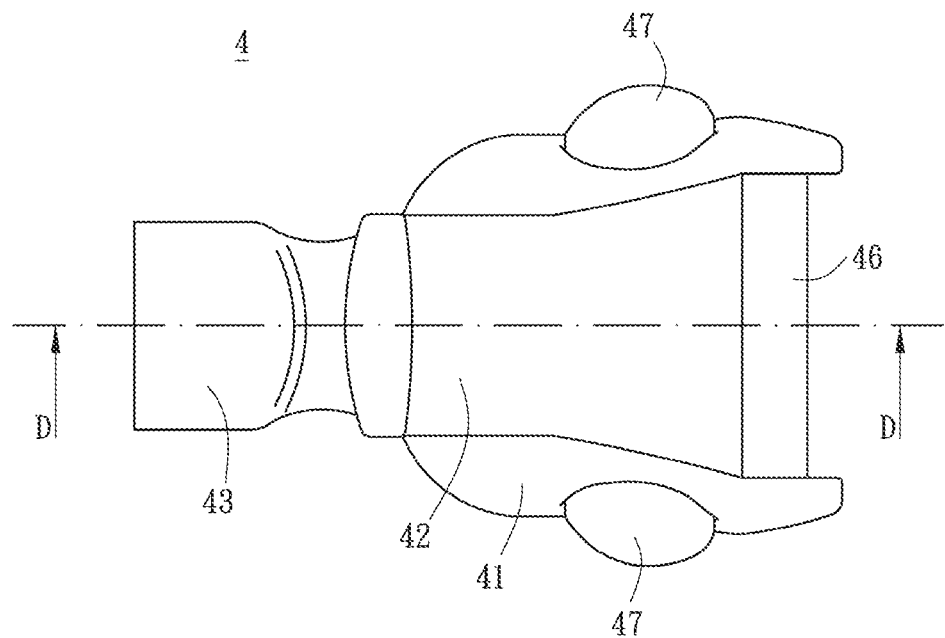
FIG. 4B is a top view of the buckling device of the second preferred embodiment of the present invention.
Figure 4C:
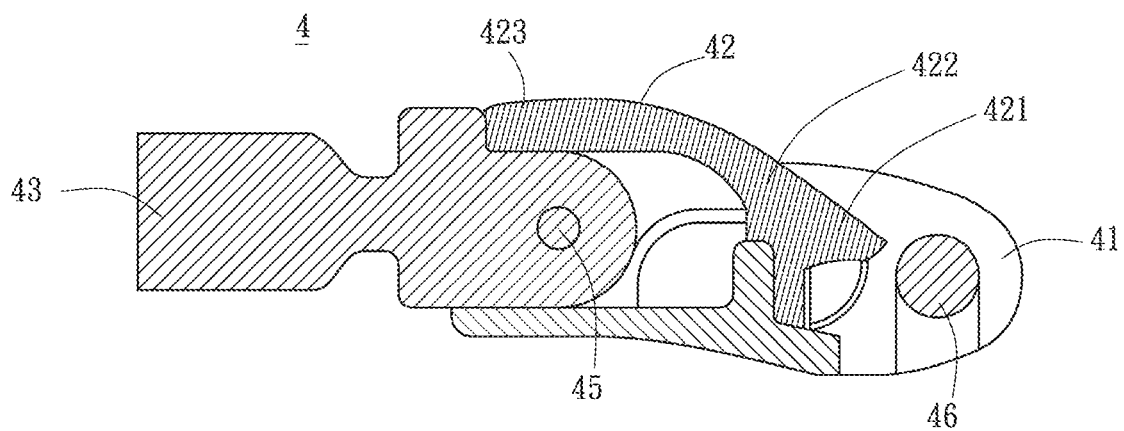
FIG. 4C is a sectional view of the second preferred embodiment of the present invention along line D-D in FIG. 4B.
Figure 4D:
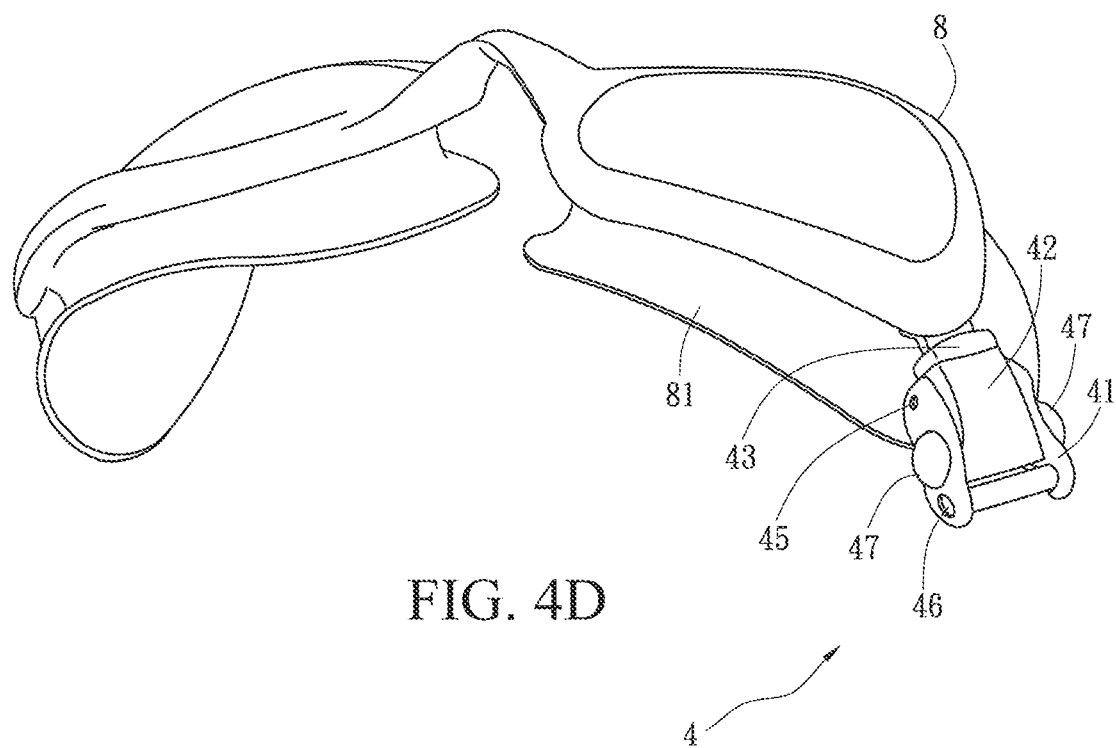
FIG. 4D is an exploded view of the buckling device of the second preferred embodiment of the present invention.
Figure 4E:
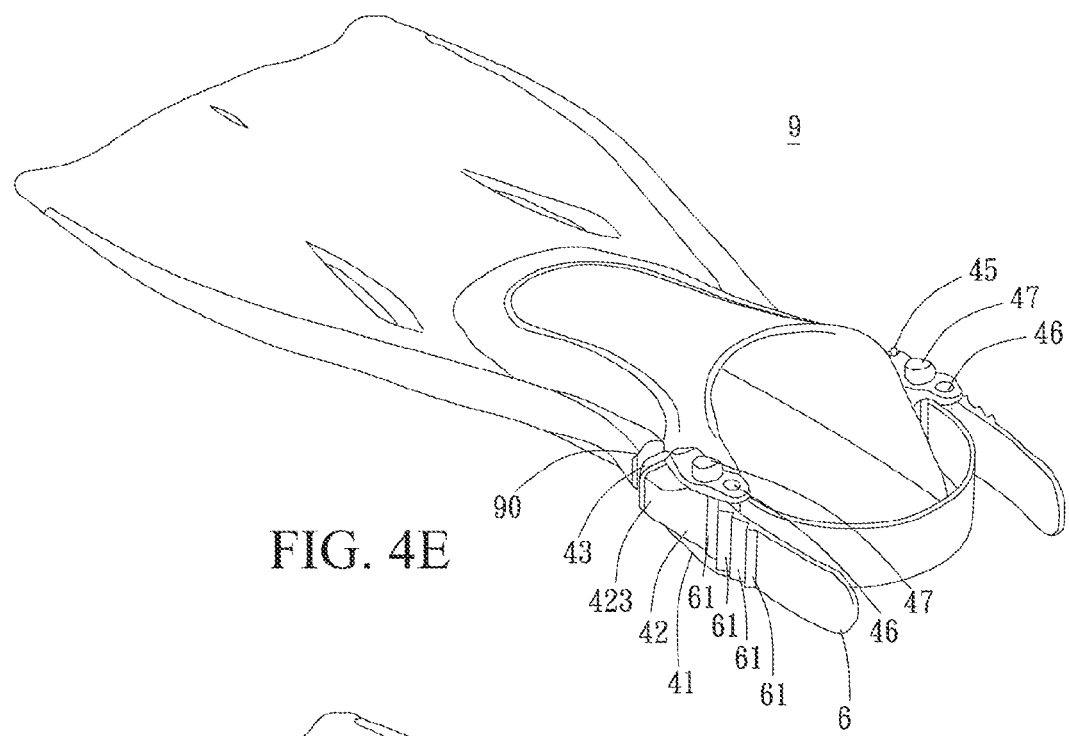
FIG. 4E is a perspective view of the buckling device of the second preferred embodiment used on a diving fin in accordance with the present invention.
Figure 4F:
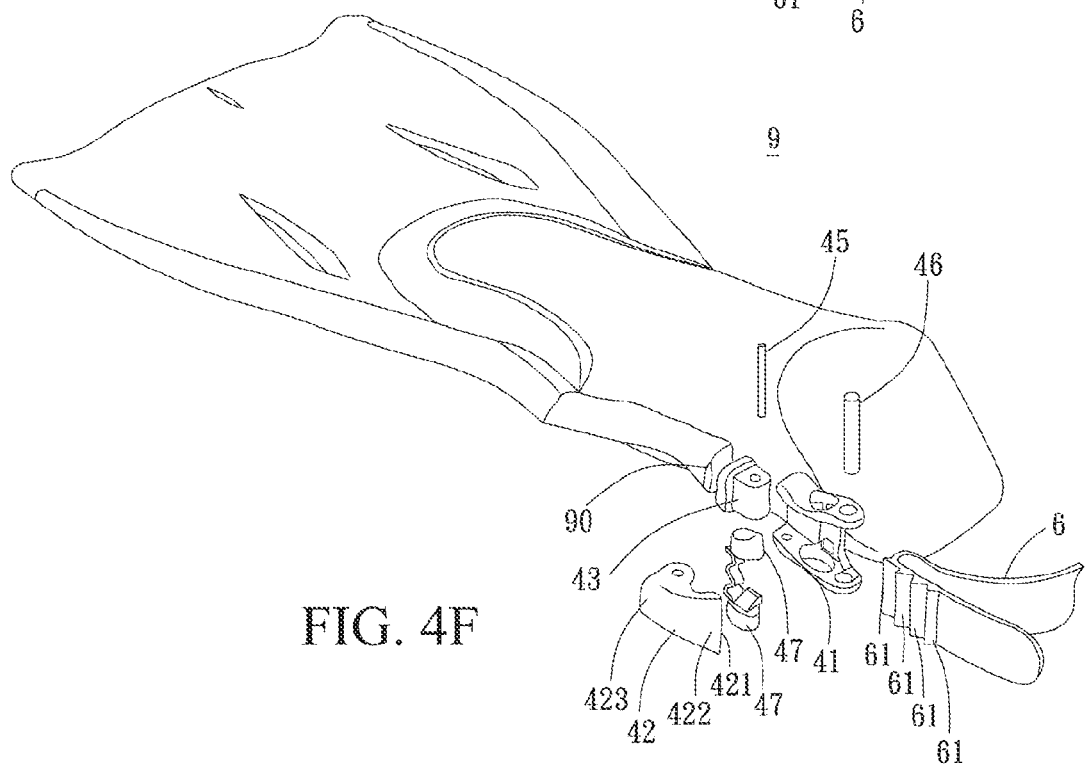
FIG. 4F is an exploded view of the second preferred embodiment used on a diving fin in accordance with the present invention.

FIGS. 4E to 4F show the buckling device 4 for the belt 6 of the second embodiment. In simultaneous reference to FIGS. 4C, 4E and 4F, the buckling device 4 further comprises a first pivot 45 and a second pivot 46. The second pivot 46 and the first portion 41 are fixed together and the belt 6 winds around the second pivot 46. A plurality of the second protrusion 61 of the belt 6 and the second pivot 46 are arranged in parallel to the first pivot 45. The second portion 42 of the buckling device 4 has an engaging end 422 and an opposite end 423. At least one first protrusion 421 is disposed on the engaging end 422 of the second portion 42. The first portion 41, the second portion 42 and the elastic portion 43 are pivotally connected by means of the first pivot 45, such that the second portion 42 and the elastic portion 43 are adapted to rotate about the first portion 41. The difference between the first preferred embodiment and the second preferred embodiment is that the buckling device 4 of the second preferred embodiment further comprises at least one push portion 47, and in this embodiment the buckling device 4 comprises two push portions 47. The push portions 47 are disposed at two lateral sides of the second portion 42 along the axial direction of the second pivot 46, as shown in FIGS. 4A and 4B.

When the two push portions 47 are simultaneously subjected to a respective pushing force and are moved inwards, the push portions 47 urge the engaging end 422 of the second portion 42 to rotate outwards about the first pivot 45. In that instant, the gap between the first protrusion 421 disposed on the engaging end 422 and the belt 6 increases, and the second protrusion 61 of the belt 6 is appropriately released. In that instant, the wearer can adjust the length of the belt 6 such that the mask 8 (as shown in FIG. 4D) or the diving fin 9 (as shown in FIGS. 4E and 4F) etc. is appropriately secured to the wearer. The engaging end 422 rotates outwards along the first pivot 45, and in that instant, when the first protrusion 421 releases the second protrusions 61, the opposite end 423 rotates inward along the first pivot 45 to press against the elastic portion 43, and an elastic restoration force is stored. When the wearer releases the pushing force exerted onto the push portions 47, the opposite end 423 subjected to the restoration force of the elastic portion 43 rotates outwards along the first pivot 45 such that the engaging end 422 rotates inwards along the first pivot 45 and restores to its initial position. Therefore, the first protrusion 421 disposed on the engaging end 422 re-engages with the second protrusion 61 of the belt 6 such that the second protrusion 61 of the belt 6 is subjected to the engagement of the first protrusion 421.

Figure 5A:
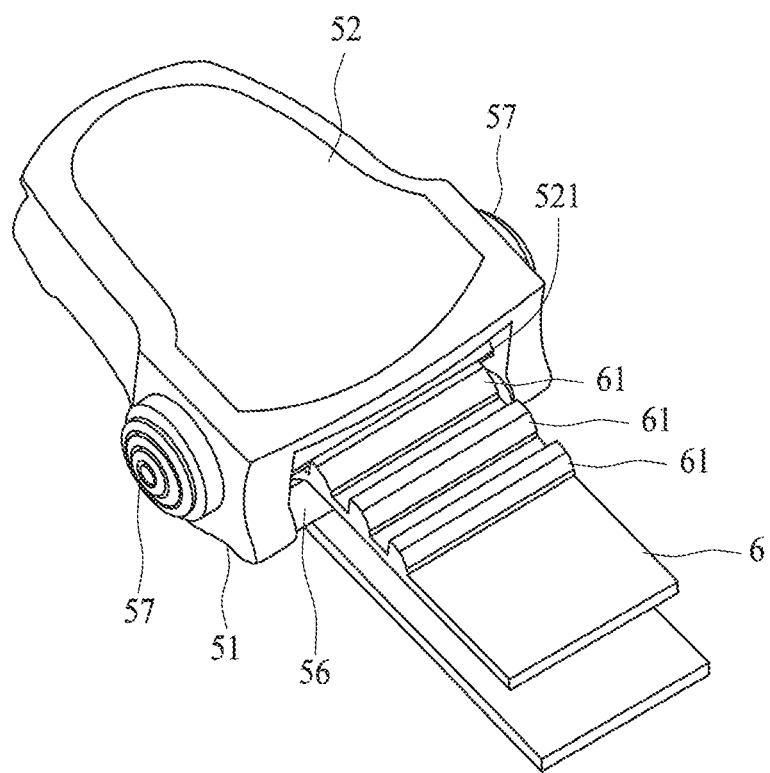
FIG. 5A is a perspective view of a buckling device of a third preferred embodiment of the present invention.
Figure 5B:
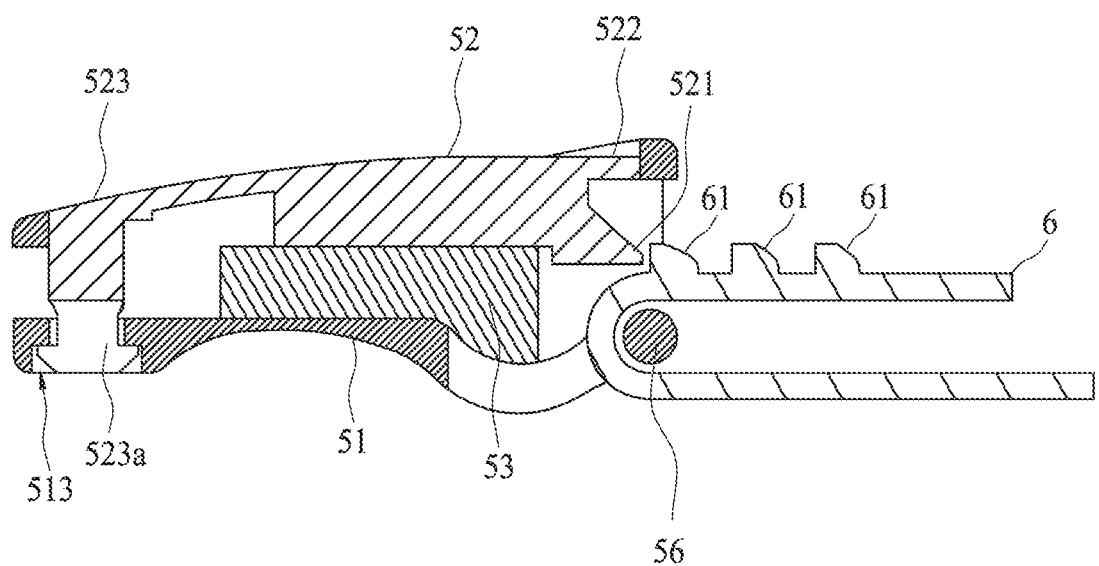
FIG. 5B is a sectional view of the buckling device of a third preferred embodiment of the present invention.
Figure 5C:
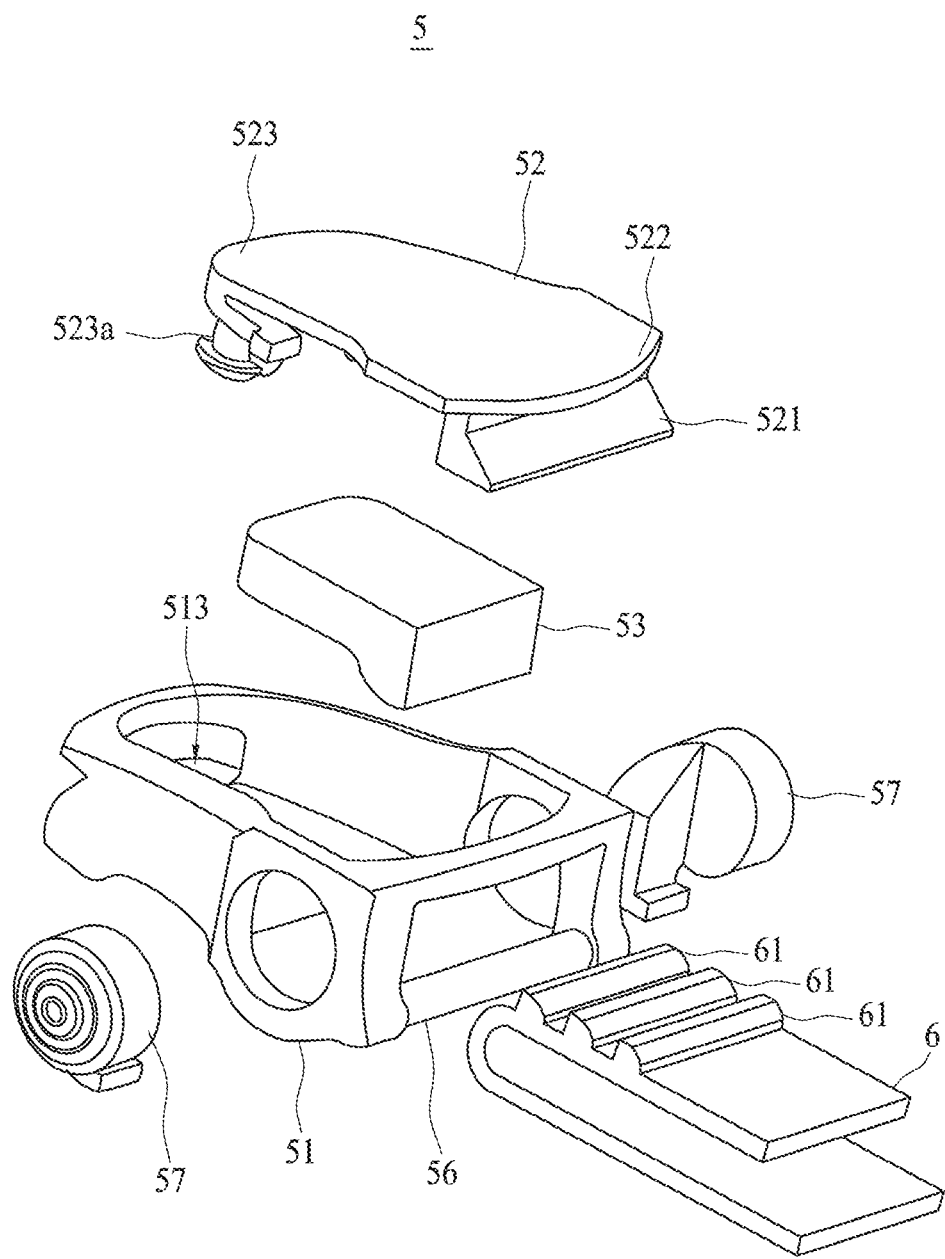
FIG. 5C is an exploded view of the buckling device of the third preferred embodiment of the present invention.

FIGS. 5A to 5C illustrate the buckling device 5 of the third embodiment of the present invention. The buckling device 5, similar to that of the first and second embodiments, also comprises a first portion 51, a second portion 52 and an elastic portion 53. The elastic portion 53 is disposed between the first portion 51 and the second portion 52, wherein the elastic portion 53 similarly has a shore hardness substantially between A10 to A95, and the elastic coefficient of the elastic portion 53 is smaller than that of the first portion 51 and is below 20 Gpa, i.e., the elastic portion 53 as opposed to the first portion 51 possess better flexibility. The selection of materials of the elastic portion 53 and the first portion 51 is similar to that of the first and second embodiments. Therefore, further description is omitted.

Again, in reference to FIGS. 5A to 5C, there is the buckling device 5 of the third embodiment of the present invention for securing a belt 6 with a plurality of second protrusions 61. The buckling device 5 further comprises a second pivot 56, which is fixed to the first portion 51, and the belt 6 winds around the second pivot 56. A plurality of the second protrusions 61 of the belt 6 are disposed in parallel to the second pivot 56. The second portion 52 of the buckling device 5 has an engaging end 522 and an opposite end 523. The engaging end 522 of the second portion 52 has a first protrusion 521, and the opposite end 523 has a snap-fitting protrusion 523a. The first portion 51 has a snap-fitting hole 513 corresponding to the snap-fitting protrusion 523a, and the snap-fitting protrusion 523a of the opposite end 523 is adapted to be inserted into the snap-fitting hole 513 to connect and secure the first portion 51 and the second portion 52. The second portion 52 and the first portion 51 both hold the elastic portion 53, and the elastic portion 53 provides a height such that in that instant the second portion 52 urges at the elastic portion 53; the first protrusion 521 appropriately engages the second protrusions 61 of the belt 6 and thus the belt 6 is fastened.

In another example of this embodiment, on the contrary, the opposite end 523 may have the snap-fitting hole 513, the first portion 51 may have the snap-fitting protrusion 523a corresponding to the snap-fitting hole 513, and the snap-fitting protrusion 523a of the first portion 51 is adapted to be inserted into the snap-fitting protrusion 523a to connect and secure the first portion 51 and the second portion 52.

The buckling device 5 further comprises at least one push portion 57, and in this embodiment the buckling device 5 comprises two push portions 57 disposed along the axial direction of the second pivot 56 at the two laterals of the second portion 52 as shown in FIGS. 5A and 5C. At the instant the two push portions 57 are subjected to pushing force and move inwards, the push portions 57 press against the elastic portion 53 to urge the elastic portion 53 to deform and protrude outwards. The protruded elastic portion 53 further outwardly holds up the engaging end 522 of the second portion 52 such that the second portion 52 is adapted to rotate outwards about the first portion 51 with regard to the snap-fitting protrusion 523a (i.e., the second portion 52 in FIG. 5B rotates counterclockwise). Thus, the gap between the first protrusion 521 disposed on the engaging end 522 and the belt 6 increases which appropriately releases the second protrusions 61 of the belt 6. In that instant, the wearer can adjust the length of the belt 6 such that the mask 8 or the diving fin 9 is appropriately fastened to the wearer. When the engaging end 522 rotates outwards with regard to the snap-fitting protrusion 523a and the first protrusion 521 releases the second protrusions 61, the elastic portion 53 and the second portion 52 subjected to a push force store an elastic restoration force. Thus, when the wearer releases the pushing force exerted onto the push portions 57, the elastic portion 53 and the snap-fitting protrusion 523a release the elastic restoration force and the protruded elastic portion 53 restores to the original shape thereof. Following the disappearance of the pushing subject to the second portion 52, the engaging end 522 rotates inwards with regard to the snap-fitting protrusion 523a (i.e., the second portion 52 in FIG. 5B rotates clockwise) to return to its original position, such that the first protrusion 521 on the engaging end 522 re-engages with the second protrusions 61 of the belt 6 such that the second protrusions 61 of the belt 6 is subjected to the engagement of the first protrusion 521.

Figure 3A:
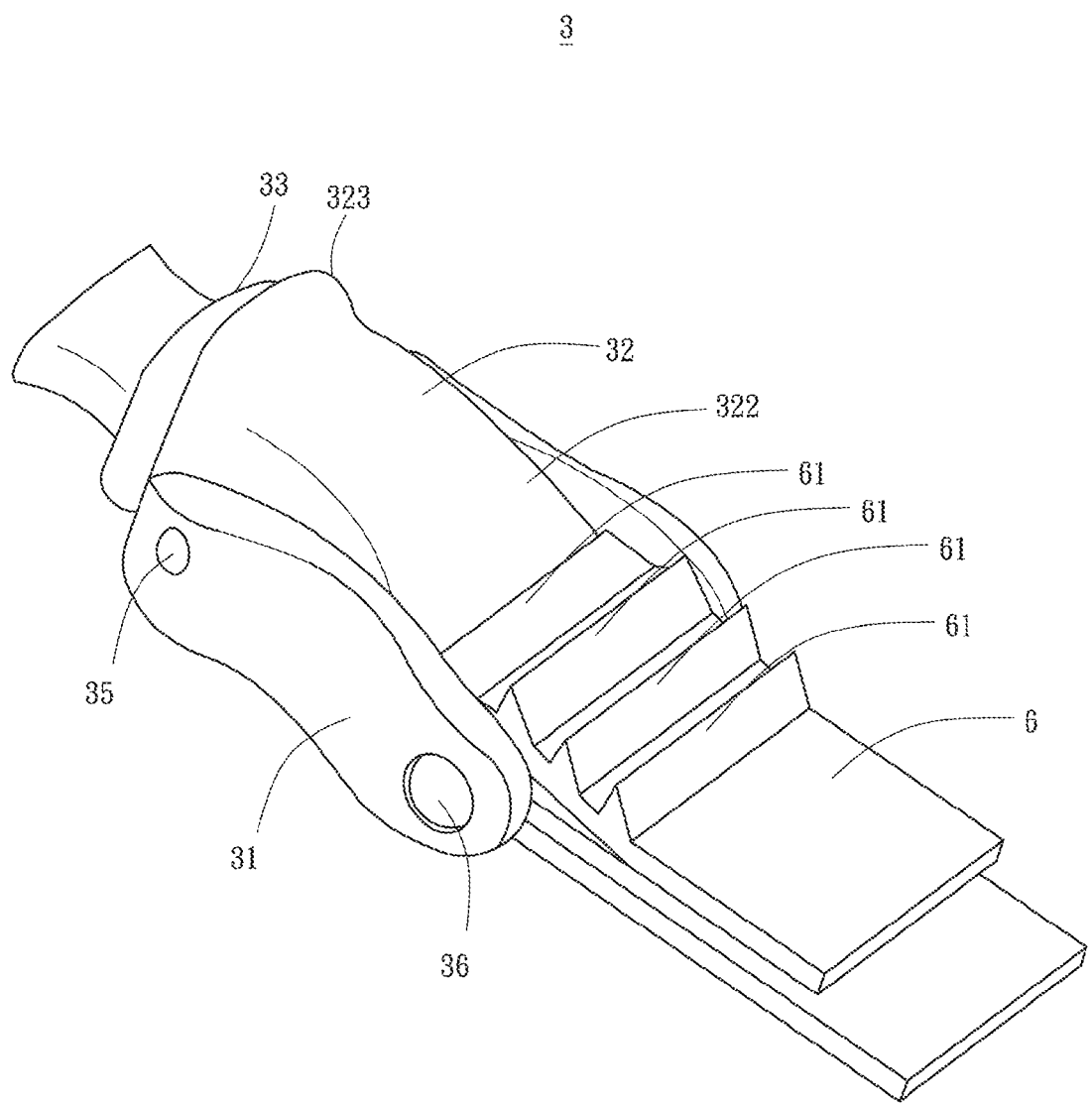
FIG. 3A is a perspective view of a buckling device of the first preferred embodiment of the present invention.
Figure 3B:
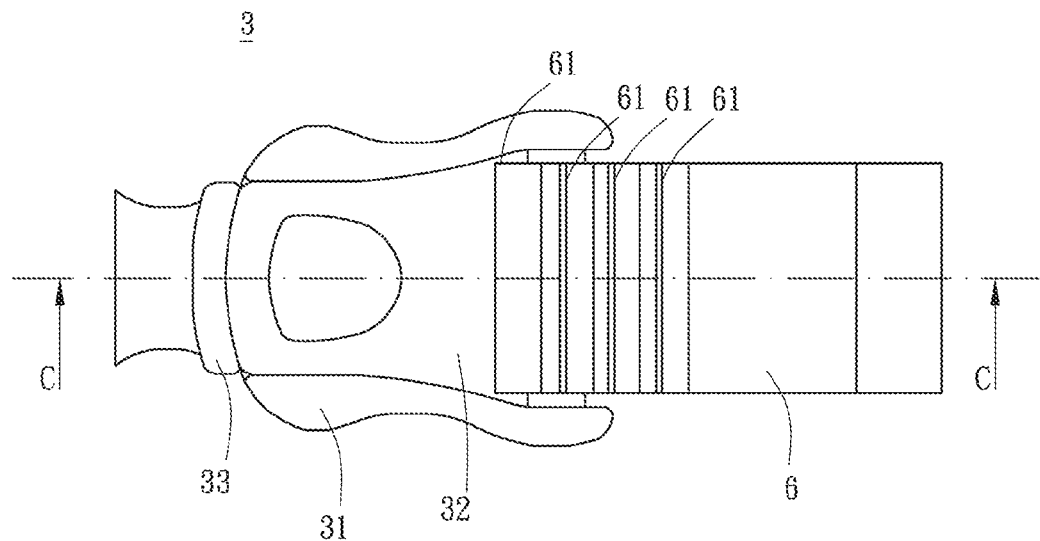
FIG. 3B is a top view of the buckling device of the first preferred embodiment of the present invention.
Figure 3C:
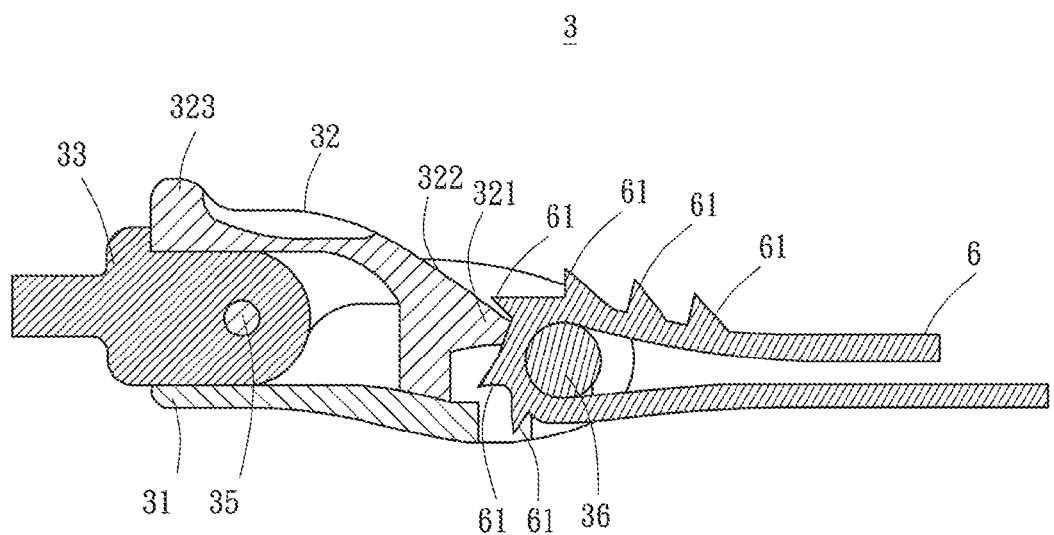
FIG. 3C is a sectional view of the first preferred embodiment of the present invention along line C-C in FIG. 3B.
Figure 3D:
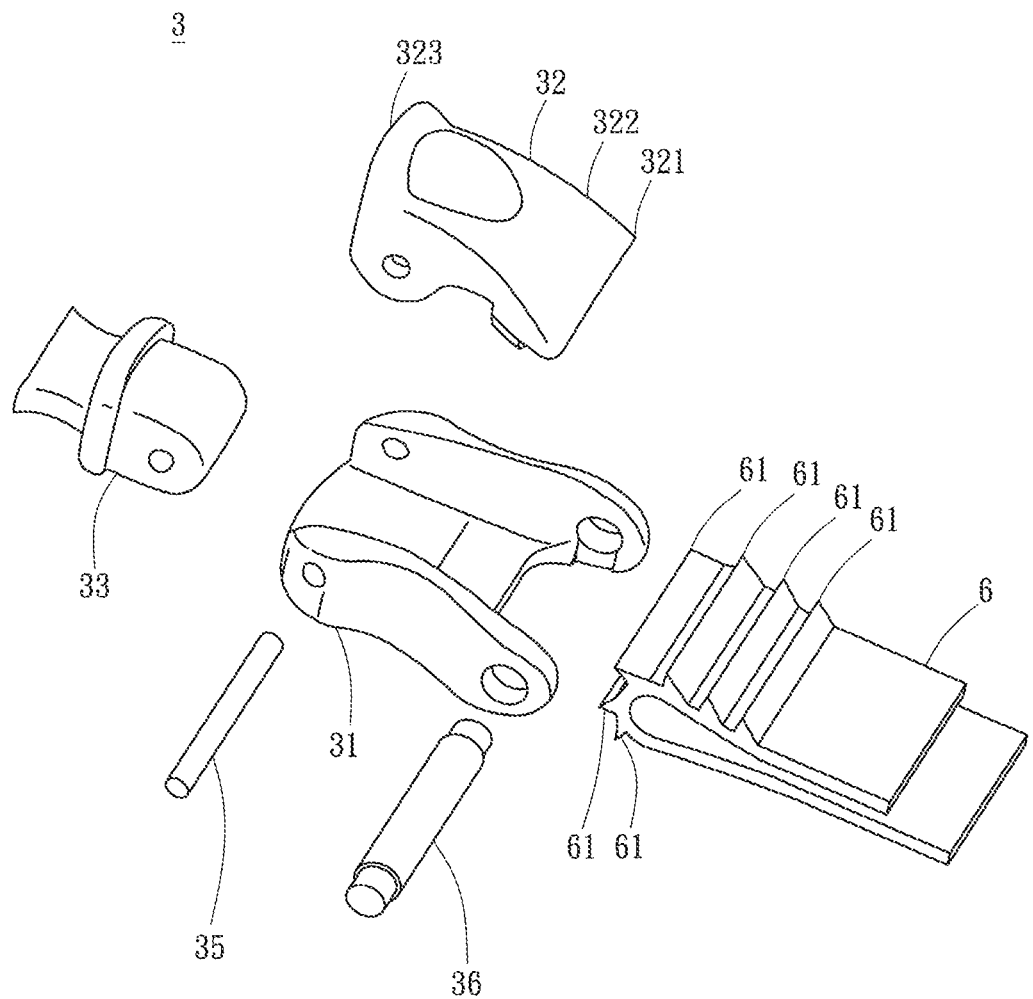
FIG. 3D is an exploded view of the buckling device of the first preferred embodiment of the present invention.
Figure 3E:
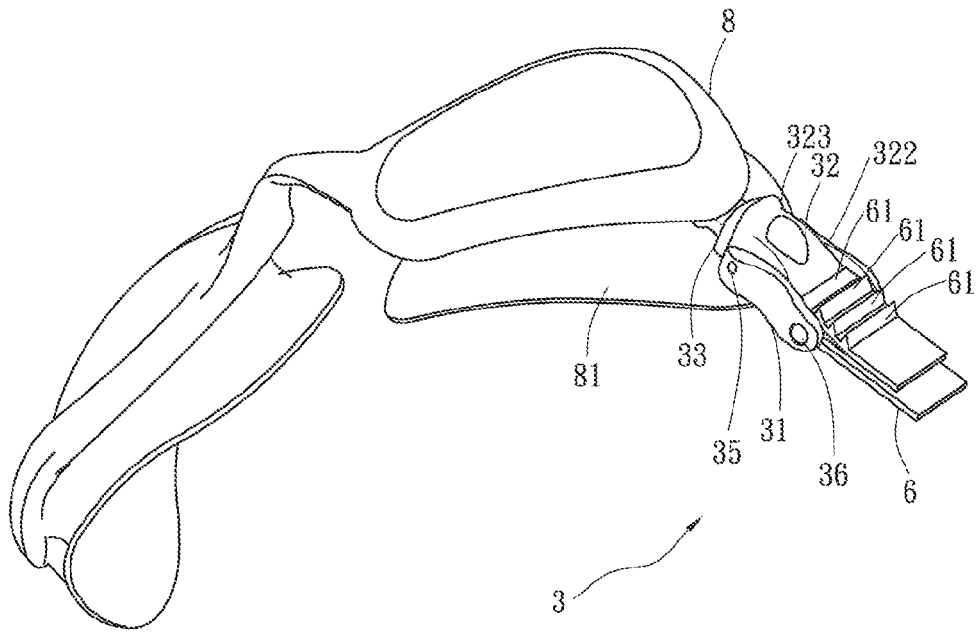
FIG. 3E is a perspective view of the buckling device of the first preferred embodiment used on a mask in accordance with the present invention.
Figure 3F:
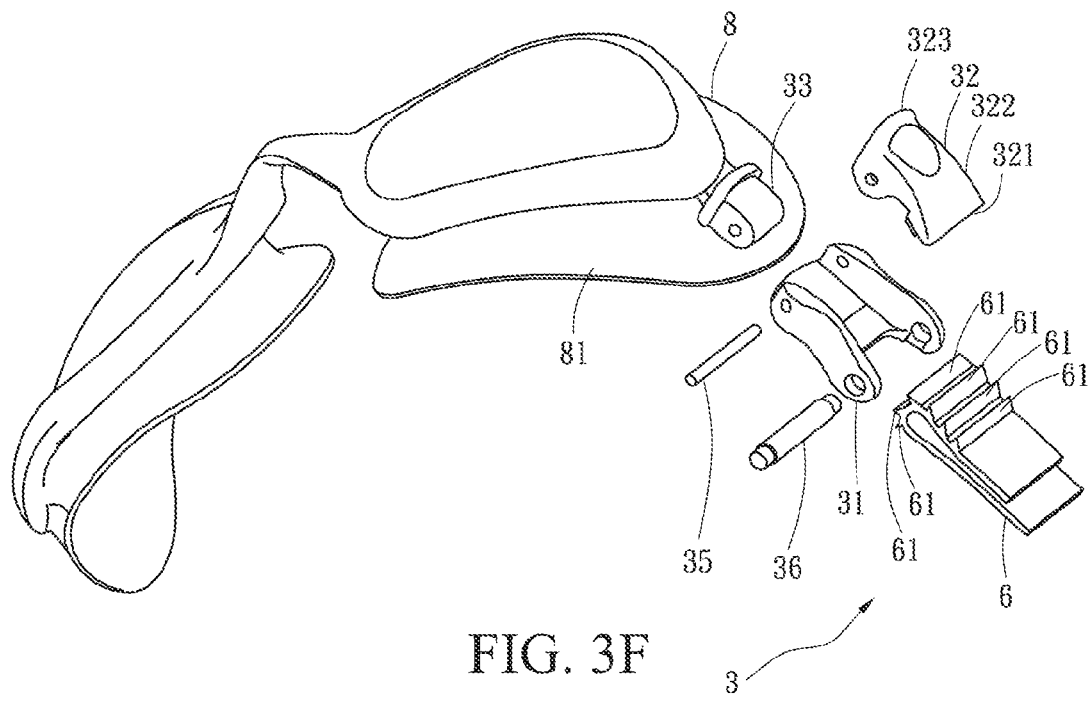
FIG. 3F is an exploded view of the first preferred embodiment used on a mask in accordance with the present invention.
Figure 3G:
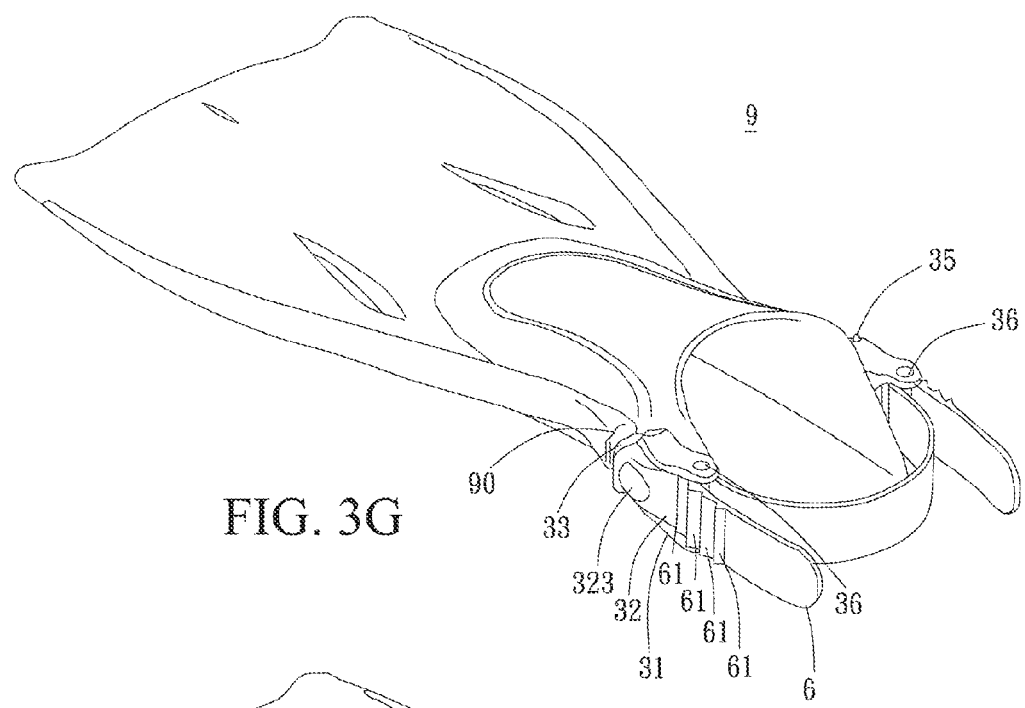
FIG. 3G is a perspective view of the buckling device of the first preferred embodiment used on a diving fin in accordance with the present invention.
Figure 3H:
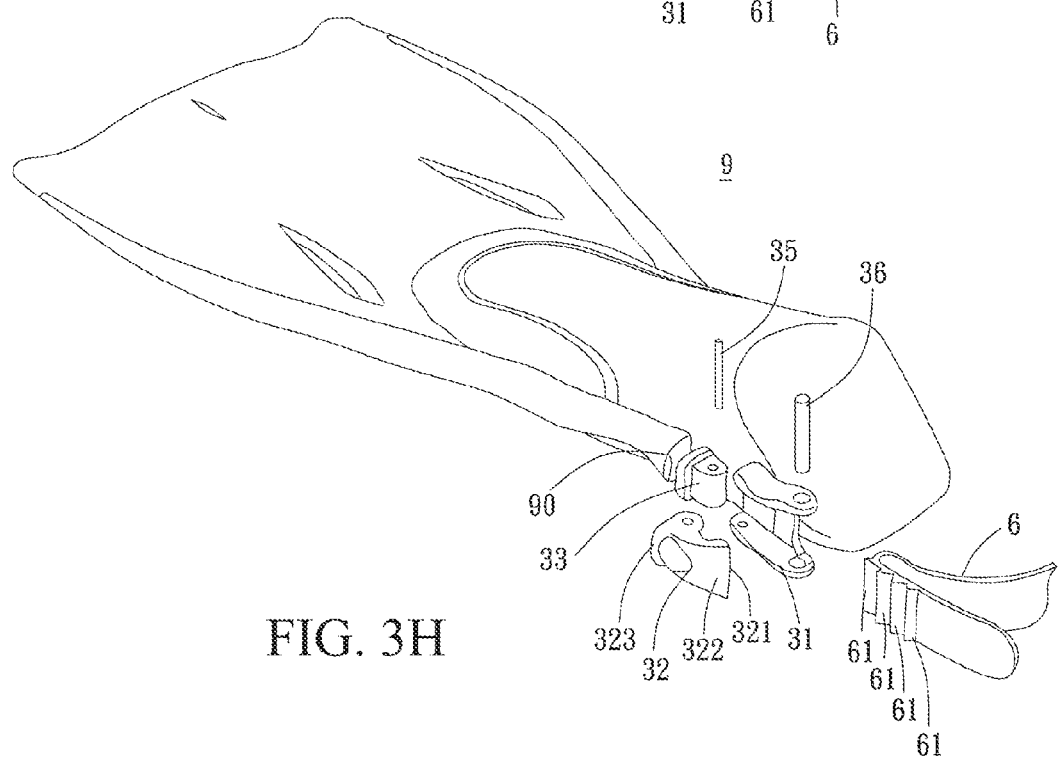
FIG. 3H is an exploded view of the first preferred embodiment used on a diving fin in accordance with the present invention.

The elastic portions 33, 43, 53 of the present invention and the soft material portions of various articles may be formed integrally. For example, as shown in FIGS. 3E, 3F and 4D, the elastic portion 33 of the first embodiment is an extension of a skirt 81 of the mask 8, and is formed integrally with the skirt 81, wherein the mask 8 can be swimming goggles, diving masks or other devices which cover the face of the wearer, however, the articles are not limited to the above-mentioned. In reference to FIGS. 3G to 3H and from FIGS. 4E to 4F, the elastic portion 33 of the present invention is extended from one lateral edge 90 disposed on a diving fin 9 which is formed integrally. The elastic portions 33, 43, 53 of the present invention are made of a material of excellent flexibility, therefore, it can be easily integrally formed with the soft material portions of the masks and the diving fins etc. Thus, the buckling devices 3, 4, 5 of the present invention do not require a spring to enhance the elastic restoration force of the buckling devices, and a complicated assembly procedure for the bucking devices is not required. Furthermore, the elastic portions 33, 43, 53 are made of a soft material with high flexibility, therefore drawbacks of elastic fatigue or breakage due to fatigue will not occur, and the wearer only requires very light strength to comfortably push the elastic portions 33, 43, 53 to operate the buckling devices 3, 4, 5. The buckling devices 3, 4, 5 of the present invention do not require hard material components of the conventional buckling devices 1, 2 as a restoration storage structure, also do not require the use of a spring, or metallic elastic components which can easily cause problems of fatigue, breakage and difficulty in deformation. Therefore, the longevity of the bucking devices is extended. It should be noted that the position, the distortion direction subjected to a force, the selection of material of the elastic portion and the article formed integrally described herein are not used to restrict the scope of the present invention.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A buckling device for fastening a belt that has a plurality of second protrusions, comprising:
    a first portion;
    a second portion having a first protrusion, an engaging end and an opposite end, the first protrusion is disposed to the engaging end, and the first protrusion of the second portion is configured to engage with the second protrusions of the belt;
    an elastic portion contacting the first portion and the second portion; and
    at least one push portions;
    wherein when the at least one push portions is pushed inward to force the elastic portion to protrude outward and the engaging end rotates outward, the first protrusion releases the second protrusions of the belt, and the elastic portion is made of a material with a shore hardness substantially between A10 and A95.

2. The buckling device as claimed in claim 1, wherein the elastic portion is made of the material selected from the group consisting of silicone, Thermoplastic Rubber (TPR), Polyvinyl Chloride (PVC) and the combination thereof.

3. The buckling device as claimed in claim 2, wherein the elastic portion is integrally formed with a skirt of a mask or a lateral of a diving fin.

4. The buckling device as claimed in claim 1, wherein the buckling device further comprises a first pivot, the second portion is pivotally connected to the first portion with the first pivot, the second portion has an engaging end and an opposite end, the first protrusion is disposed to the engaging end, and the first protrusion is adapted to rotate inward and engage with the second protrusions of the belt along the first pivot while the elastic portion biases the opposite end outward.

5. The buckling device as claimed in claim 4, wherein the elastic portion is disposed between the first portion and the second portion.

6. The buckling device as claimed in claim 5, wherein the buckling device further comprises at least one push portion, and when the at least one push portion is pushed inward to force the engaging end to rotate outward, the first protrusion releases the second protrusions of the belt and the opposite end rotates inward against the elastic portion along the first pivot.

7. The buckling device as claimed in claim 4, wherein the first pivot is pivotally connected with the elastic portion.

8. The buckling device as claimed in claim 4, wherein the buckling device further comprises a second pivot fastened with the first portion, and the belt winds around the second pivot.

9. The buckling device as claimed in claim 1, wherein the opposite end is fixed with the first portion for the first protrusion engaging with the second protrusions.

10. The buckling device as claimed in claim 9, wherein the elastic portion is disposed between the first portion and the second portion.

11. The buckling device as claimed in claim 10, wherein the opposite end has a snap-fitting protrusion, the first portion has a snap-fitting hole, and the snap-fitting protrusion is fastened with the snap-fitting hole.

12. The buckling device as claimed in claim 10, wherein the opposite end has a snap-fitting hole, the first portion has a snap-fitting protrusion, and the snap-fitting protrusion is fastened with the snap-fitting hole.

13. The buckling device as claimed in claim 1, wherein the buckling device further comprises a second pivot fastening with the first portion, and the belt winds around the second pivot.

14. The buckling device as claimed in claim 1, wherein the first portion is made of a material selected from the group consisting of Polycarbonate (PC), Alkylbenzene sulfonate (ABS), Polyoxymethylene (POM), Polypropylene (PP), Thermoplastic Rubber (TPR), Nylon, Polyethylene (PE), Polyurethane (PU) and the combination thereof.

* * * * *